United States Patent [19]
Kothrade et al.

[11] Patent Number: 6,075,107
[45] Date of Patent: Jun. 13, 2000

[54] USE OF COPOLYMERS OF N-VINYLPRROLIDONE IN PREPARATIONS OF WATER-INSOLUBLE SUBSTANCES

[75] Inventors: Stephan Kothrade, Limburgerhof; Helmut Meffert, Ludwigshafen; Gunther Berndl, Herxheim; Axel Sanner, Frankenthal; Stefan Stein, Saulheim; Volker Schehlmann, Römerberg; Folker Ruchatz, Neustadt, all of Germany

[73] Assignee: BASF Aktiengesellschaft, Germany

[21] Appl. No.: 09/073,856

[22] Filed: May 7, 1998

[30] Foreign Application Priority Data

May 7, 1997 [DE] Germany .............. 197 19 187

[51] Int. Cl.$^7$ .................................................. C08F 226/10
[52] U.S. Cl. .................. 526/264; 526/258; 526/263; 526/307.1; 526/308.5; 526/330; 526/911
[58] Field of Search .................................... 526/264, 263, 526/258, 911, 328.5, 307.1, 330

[56] References Cited

U.S. PATENT DOCUMENTS 5,008,321  4/1991  Hartmann et al. ............... 524/378
5,132,417  7/1992  Potthoff-Karl .................... 526/264
5,635,169  6/1997  Blankenburg ................... 424/70.15

FOREIGN PATENT DOCUMENTS 1481114  7/1977  United Kingdom.
2158724  11/1985  United Kingdom.

*Primary Examiner*—Fred Zitomer
*Attorney, Agent, or Firm*—Keil & Weinkauf

[57] ABSTRACT

The use of copolymers of
A) 60–99 mol % of N-vinylpyrrolidone, and
B) 1–40 mol % of a monomer selected from the group of
   b1) $C_8$–$C_{30}$-alkyl esters of monoethylenically unsaturated $C_3$–$C_8$-carboxylic acids,
   b2) N-alkyl- or N,N-dialkyl-substituted amides of acrylic acid or of methacrylic acid with $C_8$–$C_{18}$-alkyl radicals, or
   b3) vinyl esters of aliphatic $C_8$–$C_{30}$-carboxylic acids, or mixtures of these monomers, as surface-active substances in preparations of water-insoluble substances.

39 Claims, No Drawings

USE OF COPOLYMERS OF N-VINYLPRROLIDONE IN PREPARATIONS OF WATER-INSOLUBLE SUBSTANCES

The present invention relates to the use of copolymers of
A) 60–99 mol % of N-vinylpyrrolidone, and
B) 1–40 mol % of a monomer selected from the group of
  b1) $C_8$–$C_{30}$-alkyl esters of monoethylenically unsaturated $C_3$–$C_8$-carboxylic acids,
  b2) N-alkyl- or N,N-dialkyl-substituted amides of acrylic acid or of methacrylic acid with $C_8$–$C_{18}$-alkyl radicals, or
  b3) vinyl esters of aliphatic $C_8$–$C_{30}$-carboxylic acids, or mixtures of these monomers,
as surface-active substances (surfactants) in compositions of water-insoluble substances, and to compositions comprising these copolymers. The use is preferably in pharmaceutical or cosmetic compositions.

DE-A 25 14 100 describes copolymers of vinylpyrrolidone and long-chain alkyl (meth)acrylates, and terpolymers of vinylpyrrolidone, vinyl acetate and long-chain alkyl (meth)acrylates for use as emulsifiers for water-in-oil emulsions. The molar ratio of vinylpyrrolidone to carboxylic ester in the claimed copolymers is from 1:1 to 1:20, preferably from 1:1.5 to 1:10.

The use of said polymers as emulsifiers in oil-in-water emulsions is not known. The use of co- and terpolymers with a vinylpyrrolidone/carboxylic ester molar ratio greater than 1:1 in cosmetic or pharmaceutical compositions has likewise not been described.

Active ingredients for pharmaceutics and cosmetics are not always sufficiently soluble in water. An inadequate solubility of active ingredients in water means that compositions which are homogeneous and of satisfactory appearance are not obtained and, in many cases too, that the desired pharmaceutic or cosmetic effect is not optimally achieved. Active ingredients of this type must therefore be solubilized with amphiphilic ancillary substances, eg. surfactants. The bioavailability and the efficacy of the active ingredient are improved in this way.

It is an object of the present invention to provide solubilizers for pharmaceutical, cosmetic or other water-insoluble active ingredients or substances which are able to disperse the substances homogeneously and thus make the active ingredient available to a sufficient extent for absorption and distribution in the body. It was furthermore intended to provide substances which are able to stabilize oil-in-water emulsions.

We have found that this object is achieved by using the copolymers defined at the outset.

The N-vinylpyrrolidone-containing polymers are prepared by free-radical polymerization of the corresponding monomers which comprise in each case at least 60 mol % of vinylpyrrolidone.

Suitable comonomers B) are at least 1 and not more than 40 mol %, preferably 10 to 20 mol %, of a monomer selected from one of the following groups b1) to b3) or mixtures of these comonomers.

Suitable monomers b1) are $C_8$–$C_{30}$-alkyl esters of monoethylenically unsaturated $C_3$–$C_8$-carboxylic acids. Examples of suitable carboxylic acids are acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid or itaconic acid, with acrylic acid and/or methacrylic acid being preferred. Suitable alkyl radicals include cycloalkyl radicals. Esters with $C_8$–$C_{18}$-alkyl radicals are preferably employed. Examples of suitable monomers are octyl acrylate, 2-ethylhexyl acrylate, 2-ethylhexyl methacrylate, nonyl acrylate, decyl acrylate, lauryl acrylate, myristyl acrylate, cetyl acrylate, stearyl acrylate, oleyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate, oleyl methacrylate, behenyl methacrylate or tert-butylcyclohexyl acrylate.

Furthermore, suitable monomers b2) are also N-alkyl- or N,N-dialkyl-substituted carboxamides of acrylic acid or of methacrylic acid, where the alkyl radicals are $C_8$–$C_{18}$-alkyl or cycloalkyl radicals, for example N-stearylacrylamide, N-stearylmethacrylamide, N-octylacrylamide, N,N-dioctylacrylamide, N,N-dioctylmethacrylamide, N-cetylacrylamide, N-cetylmethacrylamide, N-dodecylacrylamide, N-dodecylmethacrylamide, N-myristylacrylamide, 2-ethylhexylacrylamide. In the case of the N,N-dialkylamides, C8- and Cg-alkyl radicals are preferred.

Further suitable monomers B are vinyl esters of aliphatic carboxylic acids ($C_8$–$C_{30}$-carboxylic acids). Vinyl esters of $C_8$–$C_{18}$-carboxylic acids are preferably used, for example vinyl esters of octanoic, nonanoic, decanoic, undecanoic, lauric, tridecanoic, myristic, palmitic, stearic, arachic or behenic acid or of oleic acid.

It is, of course, also possible to use mixtures of two or more carboxylic esters, carboxamides or vinyl esters as long as the total of the proportions of these comonomers does not exceed 40 mol %.

Further comonomers C) which can be used are the following copolymerizable monomers (or else mixtures thereof) (0–39 mol %, preferably 0–20 mol %, particularly preferably 0–10 mol %).

Monoethylenically unsaturated carboxylic acids having 3 to 8 carbon atoms, such as acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid. Preferably used from this group of monomers are acrylic acid, methacrylic acid, maleic acid or mixtures of said carboxylic acids. The monoethylenically unsaturated carboxylic acids can be employed in the copolymerization in the form of the free acid and, if available, the anhydrides or in partially or completely neutralized form. These monomers are neutralized preferably by using alkali metal or alkaline earth metal bases, ammonia or amines, eg. sodium hydroxide solution, potassium hydroxide solution, sodium carbonate, potassium carbonate, sodium bicarbonate, magnesium oxide, calcium hydroxide, calcium oxide, gaseous or aqueous ammonia, triethylamine, ethanolamine, diethanolamine, triethanolamine, morpholine, diethylenetriamine or tetraethylenepentamine.

Examples of further suitable comonomers C) are the $C_1$–$C_4$-alkyl esters, amides and nitriles of the abovementioned carboxylic acids, eg. methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, acrylamide, methacrylamide, N,N-dimethylacrylamide, N-tert-butylacrylamide, acrylonitrile, methacrylonitrile, dimethylaminoethyl acrylate, diethylaminoethyl acrylate, diethylaminoethyl methacrylate and the salts of the last-mentioned monomers with carboxylic acids or mineral acids, and the quaternized products.

Additionally suitable as other copolymerizable monomers C) are acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropanesulfonic acid and phosphono-containing monomers such as vinylphosphonic acid, allylphosphonic acid and acrylamidomethanepropanephosphonic acid.

Further suitable copolymerizable compounds C) are N-vinylcaprolactam, N-vinylimidazole, N-vinyl-2-methylimidazole, N-vinyl-4-methylimidazole, diallylammonium chloride, vinyl acetate and vinyl propionate. It is also possible to employ mixtures of said monomers.

The copolymers are prepared by known processes, eg. of solution, precipitation or inverse suspension polymerization using compounds which form free radicals under the polymerization conditions.

The polymerizations are normally carried out at from 30 to 200, preferably 40 to 110° C. Examples of suitable initiators are azo and peroxy compounds, and the usual redox initiator systems, such as combinations of hydrogen peroxide and reducing compounds, eg. sodium sulfite, sodium bisulfite, sodium formaldehyde sulfoxylate and hydrazine.

The copolymers have K values of at least 7 and up to 130, preferably 10 to 100, particularly preferably 10–20. The K values are determined by the method of H. Fikentscher, Cellulose-Chemie 13 (1932) 58–64 and 71–74 in aqueous solution at 25° C. with concentrations from 0.1 to 5% depending on the K value.

Said copolymers are suitable according to the invention for use as surface-active substances (surfactants) in compositions which comprise as active ingredient one or more water-insoluble substances. Water-insoluble substances for the purpose of this invention are substances which are predominantly undissolved in water under the conditions of use. This means that under the conditions of use the amount of dissolved substance is ineffective. Accordingly, the water-insoluble substances are immiscible with water under normal conditions, or do not spontaneously form a homogeneous phase with water. Water-insoluble substances for the purpose of this invention are, in particular, pharmaceutical or cosmetic active ingredients, but also active ingredients for use in crop protection compositions, furthermore veterinary medicinal active ingredients, food supplements, eg. for dietetic foods, food colorings or additives for livestock nutrition. The copolymers can moreover be used to improve the bioavailability of active ingredients which are of low solubility or are insoluble, or as solubilizers in an aqueous medium or for stabilizing aqueous dispersions such as suspensions or oil-in-water emulsions.

In the area of pharmaceutical formulations, the copolymers are suitable as a surfactant for solid drug forms for oral administration, suppositories, vaginal administration forms, drops for transmucosal administration, eye drops or ear drops, solutions of drugs, pulmonary administration forms, medicinal nail varnishes, medicinal hair care compositions, drug forms for parenteral administration, parenteral alimentary compositions, or for transdermal forms to improve the absorption of the active ingredient through the skin. Transdermal forms may be, besides creams, ointments, gels or lotions, also plasters such as nicotine plasters or, for example, plasters to administer steroid hormones, nitro compounds, analgesics, hydroxy carboxylic acids, vitamin A acid or other retinoids, antimycotics, antiinfectives, virostatics, alpha- or beta-blockers.

Cosmetic compositions are, according to the invention, compositions for skin care, hair cosmetics, nail care or for oral hygiene. The copolymers are suitable, for example, for solubilizing or stabilizing perfume oils, essential oils, essences or oily bath additives.

Compositions for crop protection comprise pesticides, herbicides, fungicides or insecticides, particularly including those compositions which are used as spraying or watering mixtures.

The copolymers are further suitable in the foodstuffs sector, for example as protective colloids or dispersing aids for food colorings of low solubility such as carotenoids.

The copolymers can likewise be employed as protective colloids in emulsion or suspension polymerization or in compositions for photography or in toners.

The copolymers can be employed in amounts of from 0.05% to 20%, preferably 0.1 to 10%, particularly preferably 0.5 to 5%, of the total weight of the composition. The compositions can be liquid, preferably aqueous, compositions or else solid or semisolid compositions. They may comprise, besides the copolymers and the water-insoluble active ingredients, also ancillary substances usual for the particular application in the amounts usual for this purpose.

EXAMPLES 1 TO 4

The polymers mentioned in the following examples were tested for the solubilizing action on the active ingredients diazepam. 1% by weight aqueous polymer solutions were employed.

| Polymer | K-value (1% in water) | Solubilization |
|---|---|---|
| Example 1 N-vinylpyrrolidone/ stearyl acrylate copolymer (90:10% by weight) | 20.0 | 185 $\mu$g/ml diazepam |
| Example 2 N-vinylpyrrolidone/ cetyl methacrylate copolymer (80:20% by weight) | 18.3 | 205 $\mu$g/ml diazepam |
| Example 3 N-vinylpyrrolidone/ vinylcaprolactam/ dodecylmethacrylamide terpolymer (60:20:20% by wt.) | 10.9 | 200 $\mu$g/ml diazepam |
| Example 4 N-vinylpyrrolidone/ vinyl stearate copolymer (90:10% by weight) | 25 | 195 $\mu$g/ml diazepam |

We claim:

1. A composition comprising at least one active ingredient and ingredient having a low solubility in water and therefore being predominantly undissolved under the conditions of use, and an effective amount of at least one polymer consisting of
   A) from 60 to 99 mol % of N-vinylpyrrolidone, and
   B) from 1 to 40 mol % of at least one monomer selected from the group of
      $b_1$) $C_8$–$C_{30}$-alkyl esters of monoethylenically unsaturated $C_3$–$C_8$-carboxylic acids,
      $b_2$) N-alkyl- and N,N-dialkyl-substituted amides of acrylic acid and of methacrylic acid with $C_8$–$C_{18}$-alkyl radicals, and
      $b_3$) vinyl esters of aliphatic $C_8$–$C_{30}$-carboxylic acids, as a surfactant.

2. The composition defined in claim 1, wherein the active ingredient is selected from the group consisting of pharmaceutically active ingredients, cosmetically active ingredients, active ingredients for crop protection, veterinary medical ingredients, food supplements and additives for livestock nutrition.

3. The composition defined in claim 1, comprising from 0.05 to 20% per weight of the polymer.

4. The composition defined in claim 1, wherein the polymer comprises the comonomer or comonomers B in an amount of from 10 to 20 mol %.

5. The composition defined in claim 1, wherein the polymer has a Fikentscher K value of from 7 to 130 in a aqueous solution comprising from 0.1 to 5% of the polymer at 25° C.

6. The composition defined in claim 1, wherein the comonomer or comonomers B is or are selected from the group consisting of stearyl acrylate, cetyl methacrylate, dodecyl methacrylamide and vinyl stearate.

7. A composition comprising at least one active ingredient, said ingredient having a low solubility in water and therefore being predominantly undissolved under the conditions of use, and an effective amount of at least one polymer consisting of
   A) at least 60 mol % of N-vinylpyrrolidone, and
   B) at least 1 mol % of at least one monomer selected from the group of
      $b_1$) $C_8$–$C_{30}$-alkyl esters of monoethylenically unsaturated $C_3$–$C_8$-carboxylic acids,
      $b_2$) N-alkyl- and N,N-dialkyl-substituted amides of acrylic acid and of methacrylic acid with $C_8$–$C_{18}$-alkyl radicals, and
      $b_3$) vinyl esters of aliphatic $C_8$–$C_{30}$-carboxylic acids, and
   C) at least one further monomer having one polymerizable double bond which is different from A) and B) and which is copolymerizable with A) and B) under conditions of a free-radical copolymerization, said further monomer or monomers being present in an amount of not more than 39 mol %,
wherein the sum of the mole percentages of components A), B) and C) is 100%, as a surfactant.

8. The composition defined in claim 7, wherein the active ingredient is selected from the group consisting of pharmaceutically active ingredients, cosmetically active ingredients, active ingredients for crop protection, veterinary medical ingredients, food supplements and additives for livestook nutrition.

9. The composition defined in claim 7, comprising from 0.05 to 20% per weight of the polymer.

10. The composition defined in claim 7, wherein the polymer comprises the comonomer or comonomers B in an amount of from 10 to 20 mol %.

11. The composition defined in claim 7, wherein the polymer has a Fikentscher K value of from 7 to 130 in a aqueous solution comprising from 0.1 to 5% of the polymer at 25° C.

12. The composition defined in claim 7, wherein the comonomer or comonomers B is or are selected from the group consisting of stearyl acrylate, cetyl methacrylate, dodecyl methacrylamide and vinyl stearate.

13. The composition defined in claim 7, wherein the comonomer or comonomers C is or comprise N-vinylcaprolactam.

14. An oil-in-water emulsion comprising at least one active ingredient, said ingredient having a low solubility in water and therefore being predominantly undissolved under the conditions of use, and an effective amount of at least one polymer consisting of
   A) from 60 to 99 mol % of N-vinylpyrrolidone, and
   B) from 1 to 40 mol % of at least one monomer selected from the group of
      $b_1$) $C_8$–$C_{30}$-alkyl esters of monoethylenically unsaturated $C_3$–$C_8$-carboxylic acids,
      $b_2$) N-alkyl- and N,N-dialkyl-substituted amides of acrylic acid and of methacrylic acid with $C_8$–$C_{18}$-alkyl radicals, and
      $b_3$) vinyl esters of aliphatic $C_8$–$C_{30}$-carboxylic acids, as a stabilizer.

15. The oil-in-water emulsion defined in claim 14, wherein the active ingredient is selected from the group consisting of pharmaceutically active ingredients, cosmetically active ingredients, active ingredients for crop protection, veterinary medical ingredients, food supplements and additives for livestook nutrition.

16. The oil-in-water emulsion defined in claim 14, comprising from 0.05 to 20% per weight of the polymer.

17. The oil-in-water emulsion defined in claim 14, wherein the polymer comprises the comonomer or comonomers B in an amount of from 10 to 20 mol %.

18. The oil-in-water emulsion defined in claim 14, wherein the polymer has a Fikentscher K value of from 7 to 130 in a aqueous solution comprising from 0.1 to 5% of the polymer at 25° C.

19. The oil-in-water emulsion defined in claim 14, wherein the comonomer or comonomers B is or are selected from the group consisting of stearyl acrylate, cetyl methacrylate, dodecyl methacrylamide and vinyl stearate.

20. A oil-in-water emulsion comprising at least one active ingredient, said ingredient having a low solubility in water and therefore being predominantly undissolved under the conditions of use, and an effective amount of at least one polymer consisting of
   A) at least 60 mol % of N-vinylpyrrolidone, and
   B) at least 1 mol % of at least one monomer selected from the group of
      $b_1$) $C_8$–$C_{30}$-alkyl esters of monoethylenically unsaturated $C_3$–$C_8$-carboxylic acids,
      $b_2$) N-alkyl- and N,N-dialkyl-substituted amides of acrylic acid and of methacrylic acid with $C_8$–$C_{18}$-alkyl radicals, and
      $b_3$) vinyl esters of aliphatic $C_8$–$C_{30}$-carboxylic acids, and
   C) at least one further monomer having one polymerizable double bond which is different from A) and B) and which is copolymerizable with A) and B) under conditions of a free-radical copolymerization, said further monomer or monomers being present in an amount of not more than 39 mol %,
wherein the sum of the mole percentages of components A), B) and C) is 100%, as a stabilizer.

21. The composition defined in claim 20, wherein the active ingredient is selected from the group consisting of pharmaceutically active ingredients, cosmetically active ingredients, active ingredients for crop protection, veterinary medical ingredients, food supplements and additives for livestook nutrition.

22. The oil-in-water emulsion defined in claim 20, comprising from 0.05 to 20% per weight of the polymer.

23. The oil-in-water emulsion defined in claim 20, wherein the polymer comprises the comonomer or comonomers B in an amount of from 10 to 20 mol %.

24. The oil-in-water emulsion defined in claim 20, wherein the polymer has a Fikentscher K value of from 7 to 130 in a aqueous solution comprising from 0.1 to 5% of the polymer at 25° C.

25. The oil-in-water emulsion defined in claim 20, wherein the comonomer or comonomers B is or are selected from the group consisting of stearyl acrylate, cetyl methacrylate, dodecyl methacrylamide and vinyl stearate.

26. The oil-in-water emulsion defined in claim 20, wherein the comonomer or comonomers C is or comprise N-vinylcaprolactam.

27. An emulsion or suspension comprising at least one active ingredient, said ingredient having a low solubility in water and therefore being predominantly undissolved under the conditions of use, and an effective amount of at least one polymer consisting of
  A) from 60 to 99 mol % of N-vinylpyrrolidone, and
  B) from 1 to 40 mol % of at least one monomer selected from the group of
    $b_1$) $C_8$–$C_{30}$-alkyl esters of monoethylenically unsaturated $C_3$–$C_8$-carboxylic acids,
    $b_2$) N-alkyl- and N,N-dialkyl-substituted amides of acrylic acid and of methacrylic acid with $C_8$–$C_{18}$-alkyl radicals, and
    $b_3$) vinyl esters of aliphatic $C_8$–$C_{30}$-carboxylic acids, as a protective colloid.

28. The emulsion or suspension defined in claim 27, wherein the active ingredient is selected from the group consisting of pharmaceutically active ingredients, cosmetically active ingredients, active ingredients for crop protection, veterinary medical ingredients, food supplements and additives for livestook nutrition.

29. The emulsion or suspension defined in claim 27, comprising from 0.05 to 20% per weight of the polymer.

30. The emulsion or suspension defined in claim 27, wherein the polymer comprises the comonomer or comonomers B in an amount of from 10 to 20 mol %.

31. The emulsion or suspension defined in claim 27, wherein the polymer has a Fikentscher K value of from 7 to 130 in a aqueous solution comprising from 0.1 to 5% of the polymer at 25° C.

32. The emulsion or suspension defined in claim 27, wherein the comonomer or comonomers B is or are selected from the group consisting of stearyl acrylate, cetyl methacrylate, dodecyl methacrylamide and vinyl stearate.

33. A emulsion or suspension comprising at least one active ingredient, said ingredient having a low solubility in water and therefore being predominantly undissolved under the conditions of use, and an effective amount of at least one polymer consisting of
  A) at least 60 mol % of N-vinylpyrrolidone, and
  B) at least 1 mol % of at least one monomer selected from the group of
    $b_1$) $C_8$–$C_{30}$-alkyl esters of monoethylenically unsaturated $C_3$–$C_8$-carboxylic acids,
    $b_2$) N-alkyl- and N,N-dialkyl-substituted amides of acrylic acid and of methacrylic acid with $C_8$–$C_{18}$-alkyl radicals, and
    $b_3$) vinyl esters of aliphatic $C_8$–$C_{30}$-carboxylic acids, and
  C) at least one further monomer having one polymerizable double bond which is different from A) and B) and which is copolymerizable with A) and B) under conditions of a free-radical copolymerization, said further monomer or monomers being present in an amount of not more than 39 mol %,
wherein the sum of the mole percentages of components A), B) and C) is 100%, as a protective colloid.

34. The emulsion or suspension defined in claim 33, wherein the active ingredient is selected from the group consisting of pharmaceutically active ingredients, cosmetically active ingredients, active ingredients for crop protection, veterinary medical ingredients, food supplements and additives for livestook nutrition.

35. The emulsion or suspension defined in claim 33, comprising from 0.05 to 20% per weight of the polymer.

36. The emulsion or suspension defined in claim 33, wherein the polymer comprises the comonomer or comonomers B in an amount of from 10 to 20 mol %.

37. The emulsion or suspension defined in claim 33, wherein the polymer has a Fikentscher K value of from 7 to 130 in a aqueous solution comprising from 0.1 to 5% of the polymer at 25° C.

38. The emulsion or suspension defined in claim 33, wherein the comonomer or comonomers B is or are selected from the group consisting of stearyl acrylate, cetyl methacrylate, dodecyl methacrylamide and vinyl stearate.

39. The emulsion or suspension defined in claim 33, wherein the comonomer or comonomers C is or comprise N-vinylcaprolactam.

* * * * *

UNITED STATES PATENT AND TRADEMARK OFFICE
CERTIFICATE OF CORRECTION

PATENT NO. : 6,075,107
DATED : June 13, 2000
INVENTOR(S) : KOTHRADE et al.

It is certified that error appears in the above-identified patent and that said Letters Patent is hereby corrected as shown below:

<u>IN THE TITLE</u>   and column 1, line 2

Page 1, Box 54, line 2, change "VINYLPRROLIDONE" to --VINYLPYRROLIDONE--

<u>IN THE CLAIMS</u>

Column 4, claim 1, line 54 change "and ingredient" to --said ingredient--.

Signed and Sealed this

Twenty-second Day of May, 2001

*Attest:*

NICHOLAS P. GODICI

*Attesting Officer*   *Acting Director of the United States Patent and Trademark Office*